United States Patent [19]

Nagata et al.

[11] Patent Number: 5,066,132

[45] Date of Patent: Nov. 19, 1991

[54] METHOD OF AND APPARATUS FOR INSPECTING PAINT COATING

[75] Inventors: Tsuyoshi Nagata, Ibaragi; Shinji Okuda, Takarazuka, both of Japan

[73] Assignee: Sunstar Engineering, Inc., Osaka, Japan

[21] Appl. No.: 564,167

[22] Filed: Aug. 8, 1990

[30] Foreign Application Priority Data

Aug. 9, 1989 [JP] Japan .................................. 1-207396
Aug. 9, 1989 [JP] Japan .................................. 1-207397

[51] Int. Cl.$^5$ ........................ G01N 21/59; G01N 21/88
[52] U.S. Cl. .................................... 356/432; 356/239; 356/443
[58] Field of Search ................ 356/432, 434, 435, 239, 356/443, 444

[56] References Cited

FOREIGN PATENT DOCUMENTS 55-140134 11/1980 Japan .................................. 356/434

Primary Examiner—Vincent P. McGraw
Attorney, Agent, or Firm—Koda and Androlia

[57] ABSTRACT

An apparatus for inspecting a coating formed on a workpiece, comprising a light emitter and a light receiver positioned on respective sides of the workpiece; an amplifier for amplifying a detection signal from the light receiver and for generating an amplified output signal; a comparator for comparing the amplified output signal with a predetermined level thereby to generate a control signal indicative of a difference between the amplified output signal and the predetermined level; a zero adjustment for adjusting the amplified output signal to a zero value; and a tuning circuit for tuning the amplified output signal, which is generated from the amplifier when the workpiece to be inspected has not yet been formed with the coating, to a predetermined tuned value. The tuning circuit is operable to vary the amplification factor of the amplifier and also to the intensity of light emitted by the light emitter. In place of the tuning circuit, an amplification factor setting citcuit may be used for sampling the light transmissivity of the workpiece and for selecting one of amplification factors according to the result of sampling. After the formation of the coating on the workpiece, the amplified output signal may decrease with a decrease of the light transmissivity of the workpiece, and the coating condition is determined depending on whether or not the amplified output signal is lower than the predetermined level.

4 Claims, 5 Drawing Sheets

METHOD OF AND APPARATUS FOR INSPECTING PAINT COATING

BACKGROUND OF THE INVENTION

1. Field of the Invention

The present invention relates to a method of and an apparatus for inspecting a paint coating applied on a workpiece in the form of a coated thin film.

2. Description of the Prior Art

During the assemblage of an automobile, and prior to the installation of a windowshield and a rear windowpane on respective window frames in the automobile, a sealing material is generally lined to a peripheral region of each windowpane. It is also a customary practice to apply a black-colored primer direct to the peripheral region of each windowpane, prior to the application of the sealing material, to form a primer undercoat for the purpose of enhancing the reliability in bonding of the subsequently formed sealant coating to the windowpane.

The Japanese Laid-open Patent Publication No. 61-242666, published Oct. 28, 1986, and applied for patent in Japan by the same assignee of the present invention, discloses an inspecting apparatus for inspecting the coating condition of the primer undercoat on the windowpane. According to this prior art inspecting apparatus, a light emitter and a light receiver are positioned on respective sides of the windowpane so that the amount of light passing through the primer-undercoated peripheral region of the windowpane, that is, the light transmissivity, can be detected by the light receiver. A light signal emerging from the light receiver and indicative of the detected light transmissivity is supplied to an amplifier where the light signal is amplified. The amplified light signal emerging from the amplifier is compared with a predetermined level by a comparator which subsequently generates a control signal according to the difference between the amplified light signal and the predetermined level.

Where the windowpane to be inspected is of a type having its peripheral region lined with black-colored ceramics to provide a so-called ceramics-lined glass, the light transmissivity as measured across the ceramics-lined peripheral region of the windowpane is extremely low, for example, lower than about 0.1%, because of the presence of the black layer of the primer undercoat and, moreover, the difference in light transmissivity between the ceramics-lined windowpane with the primer undercoat having not yet been formed thereon and the ceramics-lined windowpane with the primer undercoat having been formed is very small.

In view of the foregoing, the prior art inspecting apparatus of the type discussed hereinabove has been found ineffective to provide an accurate measurement not only because the light signal outputted from the light receiver is very low, but also because the amount of change in level of the light signals which are generated from the light receiver when the windowpane having no primer undercoat formed thereon is inspected and when the windowpane having the primer undercoat formed thereon is inspected, respectively, is very small.

In other words, while the peripheral region of the windowpane has been lined with the black-colored ceramics, the addition of the black-colored primer coating to the same peripheral region of the windowpane considerably reduces the light transmissivity of the windowpane to a value lower than that exhibited when the primer coating has not yet been formed on the windowpane. Therefore, with this type of windowpane, neither an automatic inspection of the coating condition with the use of the previously discussed prior art inspecting apparatus or an industrial television monitor system nor an inspection based on the naked eyes of a skilled inspector is possible.

SUMMARY OF THE INVENTION

The present invention has therefore been envisaged to substantially eliminating the above discussed problems and is intended to provide an improved inspecting method of and an improved inspecting apparatus which are effective to provide an accurate transmissivity measurement with respect to a workpiece having a paint coating overlaying an undercoat such as a black-colored primer coating having a relatively low light transmissivity.

In order to accomplish the above described object, the present invention provides a method of inspecting a film-like coating formed on a workpiece, which comprises positioning the workpiece between a light emitter and a light receiver so that rays of light from the light emitter can pass through the workpiece towards the light receiver; amplifying a detection signal generated from the light receiver and being indicative of the amount of light having passed through the workpiece. An amplified output signal from the amplifier is then compared with a predetermined level with the use of a comparator which generates a control signal indicative of a difference between the amplified output signal and the predetermined level. The magnitude of the amplified output signal from the amplifier is then adjusted to a zero value, when and so long as the passage of the rays of light from the light emitter towards the light receiver is intercepted, and also to a predetermined tuned value when and so long as the workpiece placed in position between the light emitter and the light receiver has the coating having not yet been formed thereon. The amplified output signal, generated from the amplifier when and after the light receiver has detected the rays of light having passed through the workpiece having the coating formed thereon, is again compared with the predetermined level by the use of said comparator.

The present invention also provides an inspecting apparatus for inspecting a film-like coating formed on a workpiece, which comprises a light emitter and a light receiver adapted to be positioned on respective sides of the workpiece, said light receiver generating a detection signal indicative of the amount of light having passed through the workpiece; an amplifying means for amplifying the detection signal from the light receiver and for generating an amplified output signal; a comparing means for comparing the amplified output signal form the amplifying means with a predetermined level and for generating a control signal indicative of a difference between the amplified output signal and the predetermined level; a zero adjusting means for adjusting the amplified output signal from the amplifier to a zero value; and a tuning means for tuning the amplified output signal from the amplifier to a predetermined tuned value.

Preferably, the tuning means referred to above may comprise an amplification factor adjustment for adjusting the amplification factor of the amplifier, and an emission control means for adjusting the intensity of light emitted by the light emitter towards the light receiver.

This tuning means is operable in response to the application of an external start signal thereto to vary the amplification factor which is taken by the amplifier during the measurement of the light transmissivity of the workpiece before the formation of the primer coating thereon, so that the output signal from the amplifier can represent the predetermined tuned value.

BRIEF DESCRIPTION OF THE DRAWINGS

In any event, the present invention will become more clearly understood from the following description of preferred embodiments therof, when taken in conjunction with the accompanying drawings. However, the embodiments and the drawings are given only for the purpose of illustration and explanation, and are not to be taken as limiting the scope of the present invention in any way whatsoever, which scope is to be determined solely by the appended claims. In the accompanying drawings, like reference numerals are used to denote like parts throughout the several views, and:

DETAILED DESCRIPTION OF THE EMBODIMENTS

Figure 1:
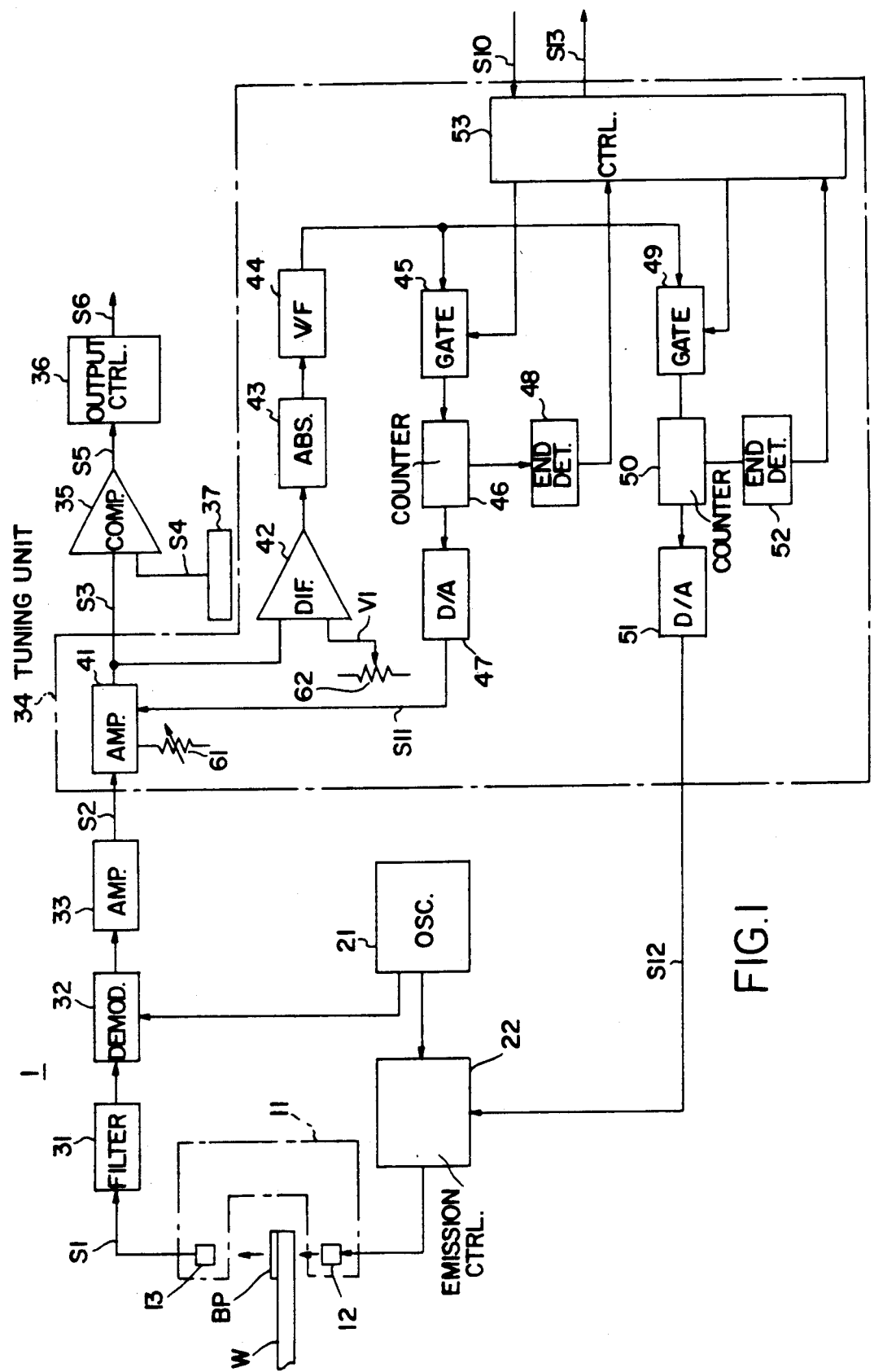
FIG. 1 is a circuit block diagram showing an inspecting apparatus according to a first preferred embodiment of the present invention.

Referring first to FIG. 1, an inspecting apparatus shown therein is so designed as to inspect a coating BP of black-colored primer, applied on a workpiece W to determine a coating condition of the primer coating BP, that is, if the primer coating BP is satisfactory or defective. This inspecting apparatus is also so designed as to provide a control signal S6 in dependence on the coating condition of the primer coating BP on the workpiece W.

So far illustrated, the workpiece W is in the form of an automobile windowpane of generally rectangular configuration and having its outer peripheral regions lined with a layer of black-colored ceramics to provide a ceramic lining. As hereinbefore discussed, the light transmissivity of the ceramics-lined peripheral region of the windowpane or workpiece W, which is expressed in terms of percentage of the amount of light passing through the ceramic lined peripheral region relative to the total amount of light projected onto the ceramics-lined peripheral region, is lower than the remainder of the windowpane or workpiece W and is generally about 0.1%. After the application of the black-colored ceramics to form the ceramic lining, the workpiece W is transported by a suitable transport means, for example, a conveyor, to a painting and inspecting station at which the black-colored primer is applied to form the primer coating BP subsequent to a tuning, as will be described later in detail, which coating BP is subsequently inspected.

The inspecting apparatus generally identified by 1 in FIG. 1 comprises a light detecting unit 11, an oscillator 21, a light emission control unit 22, a filter 31, a demodulator 32, an amplifier 33, a tuning unit 34, a comparator 35, and an output control unit 36. Although not shown, the inspecting apparatus also comprises an electric power supply unit, and a control panel having a voltmeter, manipulatable switches and display lamps all mounted thereon. This control may be a part of a housing structure accommodating therein all of the electric component parts of the inspecting apparatus, or may be a console separate from the housing structure.

The light detecting unit 11 includes a light emitter 12 and a light sensor 13 which are mounted on an arm of a manipulator of any known construction (such as disclosed in, for example, the Japanese Laid-open Patent Publication No. 61-242666 referred to hereinbefore) and are spaced a predetermined distance from each other. The light emitter 12 may comprise a light emitting diode capable of emitting infrared rays of light.

The oscillator 21 is of a type capable of generating a pulse signal having a frequency of a few KHz.

The light emission control unit 22 can be modulated by the pulse signal supplied from the oscillator 21 to provide an electric power (in the form of a pulse output) to the light emitter 12 thereby to cause the latter to emit rays of light towards the light sensor 13. This light emission control unit 22 is also operable to control the intensity of light emitted by the light emitter 12 in response to a signal S12 supplied from the tuning unit 34, the details of which will be described later.

The filter 31 is a band-pass filter capable of passing therethrough a frequency component of a detection signal S1, outputted from the light sensor 13, which is equal in frequency to a frequency component of the light emitted by the light emitter 12. The frequency component passing through the filter 31 is subsequently supplied to the demodulator 32.

The demodulation 32 is operable in synchronism with the output signal from the oscillator 21 to demodulate the output from the filter 31 into a direct current voltage signal which is proportional to the amplitude of the output from the filter 31.

The amplifier 33 is operable to amplify an output from the demodulator. It is to be noted that, although not shown, a preamplifier is in practice employed between the light sensor 13 and the filter 31.

All of the oscillator 21, the light emission control unit 22, the filter 31, the demodulator 32 and the amplifier 33 are housed within a common casing and is disposed in the vicinity of the detecting unit 11. The remaining component parts including the tuning unit 34 are housed within another casing as a main body of the inspecting apparatus, and the component parts in one casing and those in the other casing are interfaces with each other through a plurality of signal lines. The component parts housed within the second mentioned casing are also interfaced through a plurality of signal lines with a control apparatus operable to supervise and control the painting and inspecting station as a whole.

The tuning unit 34 is so designed as to be operable to vary and amplify an output signal S2 generated from the amplifier and then to generate an output signal S3 of a magnitude equal to a predetermined tuned value V1 that is determined by the tuning unit 34 as will be described later in detail.

The comparator 35 is operable to compare the output signal S3 from the tuning unit 34 with a reference voltage S4 supplied from a reference voltage generator 37 and to output an output signal S5 dependent on the difference between the output signal S3 and the reference voltage S4.

The output control unit 36 is adapted to receive the output signal S5 from the comparator 35 and then to output a control signal S6 in dependence on the output signal S5. The control signal S6 is outputted from the output control unit 36 in the event that the coating condition of the primer coating BP on the workpiece W is determined defective or unacceptable in a manner as will be described later.

Referring again to the tuning unit 34, the tuning unit 34 comprises an amplifier 41, a differential amplifier 42, an absolute value detector 43, a voltage-to-frequency (V/F) converter 44, gating circuits 45 and 49, counters 46 and 50, digital-to-analog (D/A) converters 47 and 51, end detectors 48 and 52 and a control unit 53.

The amplifier 41 has its amplification factor variable according to the magnitude of a signal S11 outputted from the digital-to-analog converter 47. This amplifier 41 is connected with a zero adjustment 61, which may be in the form of a potentiometer, for adjusting an signal S3 outputted from the amplifier 41, to a zero volt when and so long as rays of light travelling towards the light receiver 13 are intercepted.

The differential amplifier 21 is utilized to determine a tuned value V1 for the signal S3 outputted from the amplifier 41 and is operable to compare the output signal S3 with a predetermined voltage set up by a reference voltage generator 62 and then to output an output signal of a voltage proportional to the difference between the output signal S3 and the predetermined voltage.

The absolute value detector 43 is operable to output a signal indicative of the absolute value of an output voltage generated from the differential amplifier 42.

The voltage-to-frequency converter 44 is operable to output a pulse signal of a frequency (i.e., the number of pulses) proportional to the output voltage generated from the absolute value detector 43.

Each of the gating circuits 45 and 49 is adapted to be enabled by a signal supplied from the control unit 53 to allow the pulse signal from the voltage-to-frequency converter 44 to pass therethrough to the associated counter 46 or 50.

Each of the counters 46 and 50 is in the form of, for example, an up-and-down counter whose count can be selectively incremented or decremented according to the state or polarity of the output signal from the differential amplifier 42. An output signal emerging from each of the counters 46 and 50, which is indicative of the count given by the respective counter 46 or 50, is supplied to the associated digital-to-analog converter 47 or 51.

Each of the digital-to-analog converters 47 and 51 is operable to convert the output signal from the associated counter 46 or 50, which is indicative of the count given by the respective counter 46 or 50, into a respective digital signal S11 or S12 proportional to the voltage of such output signal from the associated counter 46 or 50.

Each of the end detectors 48 and 52 is operable to provide a respective end detection signal to the control unit 53 in the event that the count of the associated counter 46 or 50 exceeds a predetermined range of values controllable by the amplifier 41 or the light emission control unit 22.

The control unit 22 is utilized to control the operation of the tuning unit 34 as a whole.

A cycle of tuning operation performed by the control unit 53 will now be described.

Prior to the tuning operation being taken place, a light shielding member such as, for example, a metallic plate, is interposed between the light emitter 12 and the light receiver 13 to intercept the passage of light from the light emitter 12 towards the light receiver 13. In this condition, that is, while the passage of light from the light emitter 12 towards the light receiver 13 is intercepted in the presence of the light shielding member, the zero adjustment 61 is manipulated to set the output voltage S3 from the amplifier 41 to attain a zero volt. At this time, the amplification factor of the amplifier 41 is maximized. Upon completion of the zero adjustment, the light shielding member held between the light emitter 12 and the light receiver 13 is withdrawn, followed by a placement of the workpiece W in position between the light emitter 12 and the light receiver 13 as shown in FIG. 1.

The actual tuning is initiated when a tuning start signal S10 is inputted to the control unit 53. Although not shown, this tuning start signal S10 may be inputted to the control unit 53 from either a manipulatable start button switch or, during an automated run of the system as a whole, a central control unit used to supervise the coating and inspecting station.

With the control unit 53 receiving the tuning start signal S10, the control unit 53 provides an enable signal to the gating circuit 45 to enable the latter thereby to allow the passage of the pulse signal from the voltage-to-frequency converter 44 therethrough to the counter 46, causing the latter to perform a counting operation. The digital-to-analog converter 47 then outputs the digital signal S11 proportional to the count of the counter 46, which signal S11 is applied to the amplifier 41 so that the amplification factor of the amplifier 41 is lowered. In the event that, consequent upon the lowering of the amplification factor of the amplifier 41, the output signal S3 emerging from the amplifier 41 attains a value equal to the reference voltage set up by the reference voltage generator 62, the output voltage from the differential amplifier 42 is zeroed with no pulse signal consequently inputted to the counter 46 from the voltage-to-frequency converter 44 through the gating circuit 45, permitting the signal S3 emerging from the amplifier 41 to be tuned to the tuned value V1 thereby to complete the tuning cycle.

In the event that the mere lowering of the amplification factor of the amplifier 41 would not result in a lowering of the signal S3 to a value equal to the tuned value V1, the end detector 48 detects the arrival of the count of the counter 46 at a maximum limit thereby to generate therefrom the end detection signal to the control unit 53, causing the latter to subsequently issue control signals with which the gating circuit 45 and the gating circuit 49 are disabled and enabled, respectively. Once the gating circuit 49 is so enabled, the pulse signal emerging from the voltage-to-frequency converter 44 is supplied to the remaining counter 50 to allow the latter to start its counting operation. Then, the digital-to-analog converter 51 outputs the digital signal S12 proportional to the count of the counter 50, which signal S12 is applied to the light emission control unit 22 so that the output from the light emission control unit 22 can be lowered according to the digital signal S12. When the output from the light emission control unit 22 is so lowered, the intensity of light emitted from the light emitter 12 towards the light receiver 13 across the workpiece W is reduced. Consequent upon reduction in intensity of light emitter from the light emitter 12, the light receiver 13 outputs the detection signal S1 of a magnitude which is lowered correspondingly and, as a result thereof, the output signal S3 emerging from the amplifier 41 is lowered to a value equal to the tuned value V1, thereby completing the tuning cycle.

Should the count of the counter 50 attain a maximum limit, the arrival of the count of the counter 50 at the maximum limit is detected by the end detector 52 which subsequently issues the end detection signal to the control unit 53. The control unit 53, upon receipt of the end detection signal from the end detector 52, generates an error signal S13 indicating that the light transmissivity of the workpiece W before the primer coating BP is formed thereon, that is, the light transmissivity of the ceramics-lined glass forming the windowpane, is higher than the maximum detectable value of a predetermined detectable range in which the inspection with the apparatus of the present invention is possible. It is, however, to be noted that this error signal S13 is generated from the control unit 53 also when the light transmissivity of the ceramics-lined glass is lower than the minimum detectable value of the predetermined detectable range.

Thus, the tuning is accomplished first by adjusting the amplification factor of the amplifier 41. However, if the amplification factor of the amplifier 41 is unable to be adjusted satisfactorily because of such a circuit design limitation as hereinabove described, the tuning is then accomplished subsequently by adjusting the output from the light emission control unit 22 to adjust the intensity of light emitted by the light emitter 12. In the event that neither the adjustment of the amplification factor of the amplifier 41 nor the adjustment of the output from the light emission control unit 22 is possible because of the circuit design limitation as hereinabove discussed, the control unit 53 issues the error signal S13.

Accordingly, during a normal operation of the inspecting apparatus according to the present invention, the value (voltage) of the output signal S3 from the amplifier 41 is of a value equal to the tuned value V1 at the time of completion of the tuning cycle. In the illustrated embodiment, the tuned value V1 is preferably selected to be 400 mV. It is to be noted that, at the time the error signal S13 is outputted from the control unit 53, the amplification factor of the amplifier 41 and the output from the light emission control unit 22 assume the respective maximum or minimum value.

Regardless of the generation of the error signal S13 from the control unit 53, the operation of the inspecting apparatus of the present invention may not be interrupted and the inspection with the use of such inspecting apparatus may be continued. However, the continuance of the inspection that may be carried out subsequent to the generation of the error signal S13 from the control unit 53 may result in a reduction in reliability of the result of inspection of the coating condition of the primer coating BP on the workpiece W. Accordingly, it is rather recommended to interrupt the operation of the inspecting apparatus 1 in the event of the generation of the error signal S13. Alternatively, the error signal S13 generated from the control unit 53 may be used to activate a warning device which may be an buzzer or a display or a combination thereof.

Hereinafter, the manner in which the workpiece W is inspected with the use of the inspecting apparatus 1 embodying the present invention will be described in detail.

Subsequent to the completion of the tuning, the primer coating BP is formed on the workpiece W, specifically a peripheral region of the windowpane. After or immediately after the formation of the primer coating BP on the workpiece W, the manipulator arm carrying the detecting unit 11 is moved until that portion of the workpiece W where the primer coating BP has been formed is aligned with the path of travel of rays of light from the light emitter 12 towards the light receiver 13. Alternatively, while the detecting unit 11 is fixed in position, the workpiece W having the primer coating BP formed thereon may be moved to a position where that portion of the workpiece W can be aligned with the path of travel of rays of light from the light emitter 12 towards the light receiver 13.

Then, with the primer coating BP positioned on the path of travel of the rays of light from the light emitter 12 towards the light receiver 13, the light receiver 13 generates the detection signal S1 proportional to the light transmissivity of the primer coating BP, that is, the amount of light having passed through that portion of the workpiece W where the primer coating BP has been formed, which signal S1 is subsequently supplied to the amplifier 41 through the filter 31, then through the demodulator 32 and finally through the amplifier 33. Thus, the output signal S3 emerging from the amplifier 41 varies in proportion to the detection signal S1 indicative of the light transmissivity of the primer coating BP. The output signal S3 from the amplifier 41 and the reference voltage S4 from the reference voltage generator 37 are subsequently compared by the comparator 35 with each other, and the comparator 35 then generates the difference signal S5 indicative of the difference between the output signal S3 and the reference voltage S4.

The reference voltage S4 is determined empirically on the basis of results of experimental tests conducted on a certain number of samples and is, in the instance now under discussion, selected to be 1/5 to ½ of the tuned value V1 generated by the reference voltage generator 62. In such case, should the light transmissivity of the workpiece W be reduced to a value lower than 20 to 50% consequent upon the formation of the primer coating BP on the workpiece, the coating condition of the primer coating BP on the workpiece W is deemed satisfactory or acceptable.

The control unit 36 generates the control signal S6 only when the coating condition of the primer coating BP on the workpiece W is found defective or unacceptable. For this purpose, the control unit 36 is so controlled that no control signal is generated therefrom at any timing other than the timing at which traces of coating effected to form the primer coating BP have been left on the workpiece W is inspected.

Figure 2:
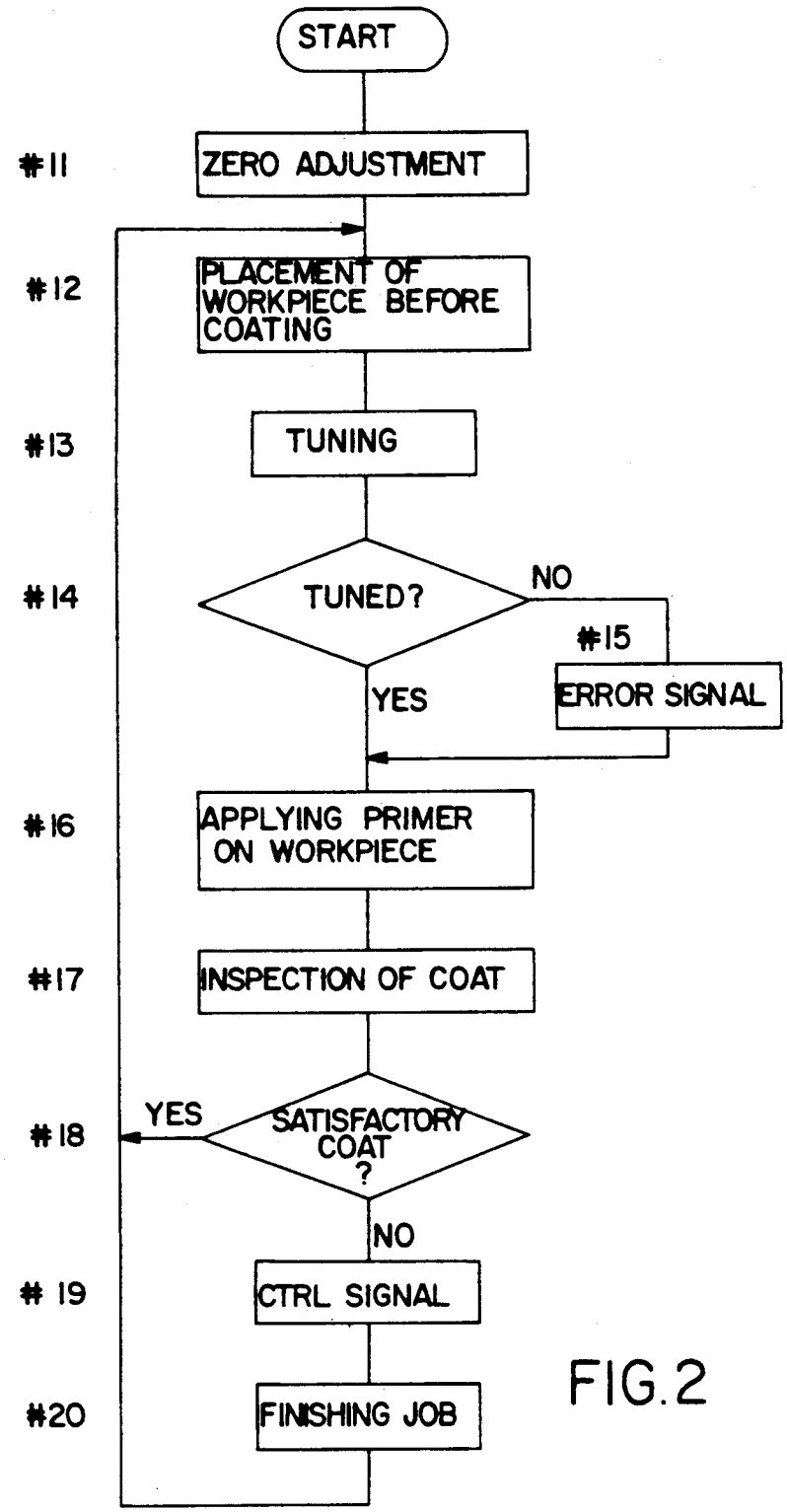
FIG. 2 is a flowchart showing a cycle of operation of the inspecting apparatus shown in FIG. 1.

Referring now to FIG. 2, there is shown a flowchart illustrating a cycle of overall operation of the inspecting apparatus 1 embodying the present invention.

Subsequent to the start of inspection, the zero adjustment is carried out at step #11. As hereinbefore described, the zero adjustment is carried out while the light receiver 13 is shielded from rays of light. Then at step #12, the workpiece W having the primer coating BP having not been formed thereon is placed in position between the light emitter 12 and the light receiver 13, followed by the tuning operation at step #13.

Should it be found at step #14 that, consequent upon the tuning, the light transmissivity of the workpiece W exceeds the detectable range, the error signal S13 is generated at step #15 from the control unit 53. On the other hand, should the tuning be accomplished satisfactorily as represented by "YES" at step #14, or subsequent to the generation of the error signal S13 from the control unit 53 at step #15 (In this case, the amplification factor of the amplifier 41 and the output from the light emission control unit 22 remain the same as those assumed when the error signal S13 has been generated from the control unit 53.), the primer coating BP is formed on the workpiece at step #16.

The flow then goes to step #17 at which the coating condition of the primer coating BP on the workpiece W is inspected. At this time, the detecting unit 11 is, while that portion of the workpiece W where the primer coating BP has been formed is positioned between the light emitter 12 and the light receiver 13, moved along the direction in which traces of coating to form the primer coating BP have been left on the workpiece W. Should the result of inspection at step #18 indicate that the coating condition of the primer coating BP on the workpiece W is not satisfactory, the control signal S6 is generated from the output control unit 36 at step #19, followed by an execution at step #20 of a finish job which may include an inspection of one or both of the workpiece W and a coating apparatus (not shown), the removal of the workpiece W having the defective primer coating BP formed thereon and other procedures necessary to permit the inspecting apparatus to initiate the next succeeding cycle of operation.

On the other hand, should the result of inspection at step #18 indicate that the coating condition of the primer coating BP on the workpiece W is satisfactory, the flow returns to step #12 to initiate the next succeeding cycle of inspection with respect to another similar workpiece.

Thus, the inspecting apparatus 1 according to the first preferred embodiment of the present invention is so designed that the amplification factor of the amplifier 41 can be varied according to the light transmissivity which may in turn vary with the type of the workpiece W to facilitate the tuning of the output signal S3 from the amplifier 41 to attain a value equal to the tuned value V1. Therefore, even with the ceramics-lined glass having a relatively low light transmissivity, the inspection of the coating condition can be carried out satisfactorily and effectively. Moreover, a similar inspection of the coating condition can also be accomplished even with the workpieces W having a relatively wide range of light transmissivity. Where the satisfactorily and effective inspection of the coating condition cannot be attained merely by the adjustment of the amplification factor of the amplifier 41, the output from the light emission control unit 22 is then varied to vary the intensity of rays of light emitted by the light emitter 12 towards the light receiver 13 and, therefore, the inspection of the coating condition of the workpieces W having a relatively wide range of light transmissivity can be achieved satisfactorily and effectively.

It is to be noted that, in the foregoing description made in connection with the first preferred embodiment of the present invention, the tuned value V1 has been described as chosen to be 400 mV. However, any suitable value other than this specific value may be chosen for the tuned value V1 in the practice of the present invention. It is also to be noted that one or both of the zero adjustment and the adjustment of the amplification factor of the amplifier 33 may be performed. Although the output signal S3 from the amplifier 41 when zeroed has been described as being zero volt, the zeroing of the output signal S3 from the amplifier 41 may be of any suitable value other than the zero volt. It may also occur to those skilled in the art to employ a suitable arrangement by which the zeroing can be automatically performed.

The inspecting apparatus of the construction described hereinbefore may be used as an instrument for measuring the light transmissivity. Where the inspecting apparatus 1 is desired to be made available as the transmissivity measuring apparatus, the use should be made of a reference filter of known light transmissivity in place of the workpiece W when the tubing is desired to be performed and, upon and subsequent to the completion of the tuning so performed, a workpiece W of which light transmissivity is desired to be measured should be replaced with the reference filter. Then, the measurement of the voltage of the output signal S3 outputted from the workpiece W as a result of the passage of rays of light from the light emitter 12 to the light receiver 13 across the workpiece W will result in an indication of the ratio of the light transmissivity of the workpiece relative to that of the reference filter.

For the inspecting apparatus 1 to be available as the transmissivity measuring apparatus, the apparatus may be equipped with one or more switches or a keyboard having numeric input keys for inputting the light transmissivity of the reference filter, an arithmetic unit for the calculation of the ratio of transmissivity and a display device of the display of inputted values and also of the calculated ratio.

Figure 3:
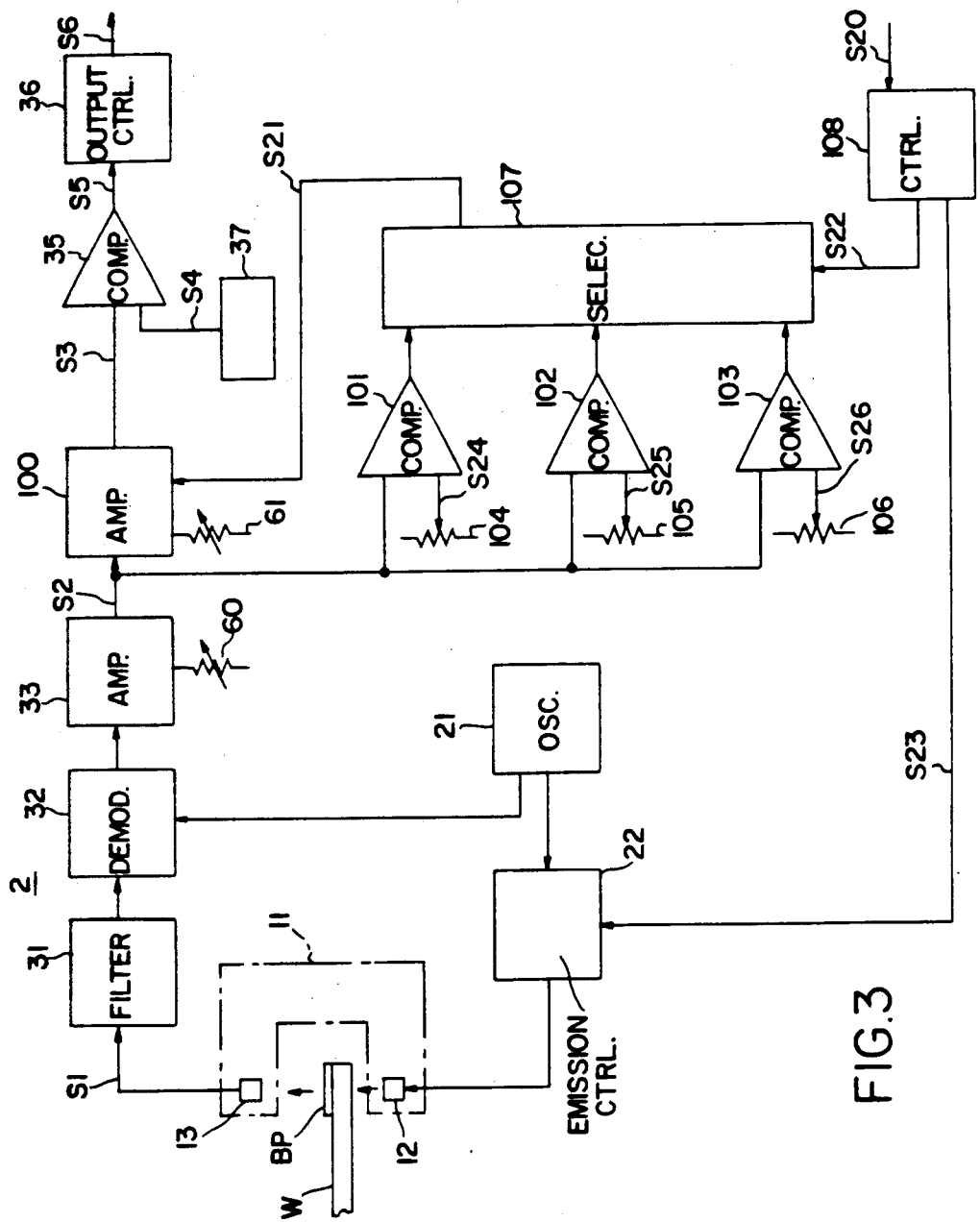
FIG. 3 is a circuit block diagram showing the inspecting apparatus according to a second preferred embodiment of the present invention.
Figure 4:
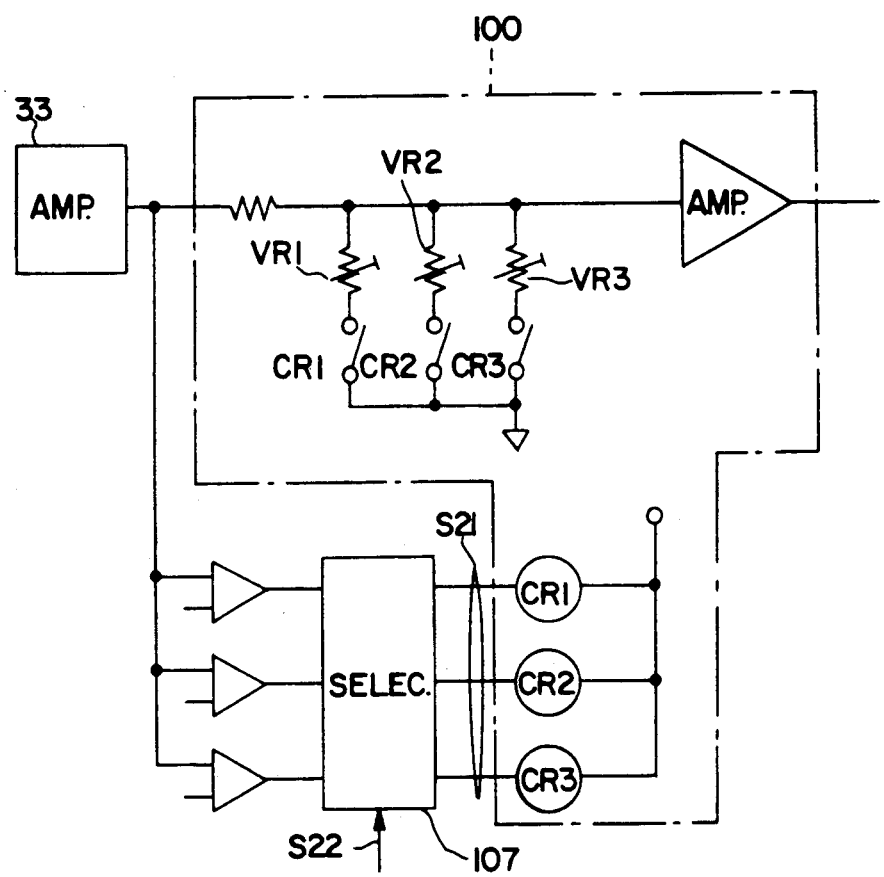
FIG. 4 is an electric circuit diagram showing the details of an amplifier employed in the inspecting apparatus shown in FIG. 3.
Figure 5:
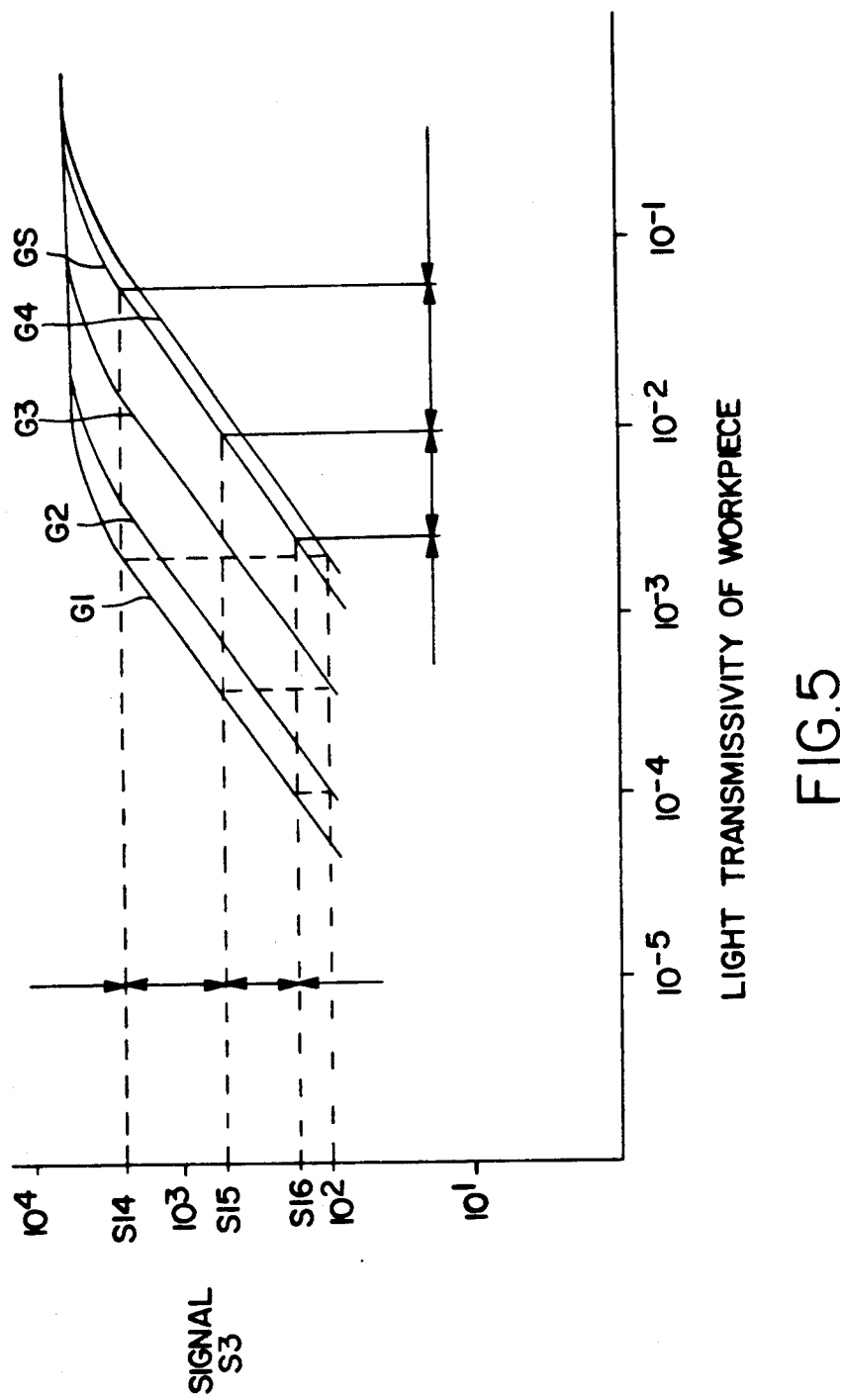
FIG. 5 is a graph showing the relationship between the light transmissivity of a workpiece and an output signal S3 outputted from an amplifier employed in the inspecting apparatus of the present invention.

Reference is now made to FIGS. 3 to 5 which illustrate a second preferred embodiment of the present invention. It is however to be noted that, in FIG. 3, components of the inspecting apparatus, now generally identified by 2, which are similar in function to the components described with respect to the inspecting apparatus 1 according to the first preferred embodiment of the present invention will be referred to with like reference numerals.

The inspecting apparatus 2 according to the second preferred embodiment of the present invention differs from the inspecting apparatus 1 according to the foregoing first preferred embodiment, instead of the use of the tuning unit 34 used in the inspecting apparatus 1, a circuit comprising an amplifier 100, comparators 101, 102 and 103, reference voltage generators 104, 105 and 106, an amplification factor selector 107 and a control unit 107 is employed.

The amplifier 100 is operable to variably amplify the output signal S22 applied thereto from the amplifier 33. The amplification factor of the amplifier 100 is selected to be one of four amplification factors according to an amplification factor signal S21 applied thereto from the amplification factor selector 107. This amplifier 100 includes the zero adjustment 61 for adjusting the output signal S3 emerging from the amplifier 100 to a zero volt when and so long as the light receiver 13 is shielded from rays of light.

Respective operations of the comparators 101 to 103, the amplification factor selector 107 and the control unit 108 will be discussed in connection of a sampling operation which is performed thereby and which will now be described.

Prior to the sampling operation being taken place, the zero adjustments 60 and 61 are adjusted to render the respective output signals S2 and S3 of the amplifiers 33 and 100 to be a zero volt while the light receiver 13 is completely shielded from the rays of light emitted by the light emitter 12 by the intervention of a metallic plate between the light emitter 12 and the light receiver 13. At this time, the amplification factor of the amplifier 10 is of the maximum value. After the completion of the zero adjustment, the metallic plate is removed and the workpiece W having the primer coating BP having been not yet formed thereon is placed in position between the light emitter 12 and the light receiver 13.

The sampling operation is carried for the purpose of detecting the light transmissivity of the workpiece W and then setting in the amplifier 100 an amplification factor proportional to the detected light transmissivity. This sampling operation is initiated simultaneously or substantially simultaneously with the entry of a sampling start signal S20 into the control unit 108. In response to the sampling start signal S20, the control unit 108 control the operation of an amplification factor selector 107 and an output condition of the light emission control unit 22.

More specifically, when the sampling start signal S20 is inputted to the control unit 108, a signal S23 necessary to lower the output from the light emission control unit 22 down to a predetermined level is outputted from the control unit 108, which signal S23 is supplied to the light emission control unit 22 to cause the intensity of light emitted by the light emitter 22 to attain a sampling intensity which is of a value lower than the intensity of light emitted by the light emitter 12 during the inspection, that is, during the detection of the light transmissivity of the workpiece W.

Under this condition, the output signal S2 emerging from the amplifier 33 is supplied to the comparators 101 to 103 each of which in turn determines the level of the input signal S2 received thereby.

Specifically, each of the comparators 101 to 103 compares the output signal from the amplifier 33 with a respective predetermined voltage S24, S25 or S26 generated from the associated reference voltage generator 104, 105 or 106 to subsequently supply to the amplification factor selector 107 a difference signal proportional to the difference between the output signal S2 and the respective predetermined voltage S24, S25 or S26.

The output signal S2 supplied from the amplifier 33 to the comparators 101 to 103 can be divided into the following four levels if the predetermined voltage S24 generated from the reference voltage generator 104 is higher than the predetermined voltage S25 generated from the reference voltage generator 105 which is in turn higher than the predetermined voltage S26 generated from the reference voltage generator 106 (i.e. S24>S25>S26).

| Level 4 | S2 > S24 |
| Level 3 | S24 ≧ S2 > S25 |
| Level 2 | S25 ≧ S2 > S26 |
| Level 1 | S26 ≧ S2 |

The level 1 signifies that the light transmissivity is minimum and, therefore, the amplifier 100 can be controlled to have the maximum amplification factor.

The control unit 108 generates a control signal S22 a predetermined time after the generation of the control signal S23, which signal S22 is supplied to the amplification factor selector 107 to allow the latter to receive the respective difference signals from the comparators 101 to 103. Subsequent to the receipt of the difference signals from the respective comparators 101 to 103, the amplification factor selector 107 outputs to the amplifier 100 an amplification factor signal S21 with which the amplification factor of the amplifier 100 is determined. The amplification factor selector 107 is a type of latch circuit designed to output one of four status values, based on the respective difference signals from the comparators 101 to 103, in response to receipt of the control signal S22 applied thereto from the control unit 108, and then to retain such one of the four status values.

Thus, the amplifier 100 can have one of four amplification factors in dependence on the amplification factor signal S21 supplied from the selector 107 to the amplifier 100, the detail of said amplifier 100 being best shown in FIG. 4.

Referring to FIG. 4, the amplifier 100 comprises a plurality of, for example, three, relay devices CR1, CR2 and CR3, and voltage dividing resistors VR1, VR2 and VR3 connected in series with make contacts of the relay devices CR1 to CR3, respectively. This amplifier 100 is so designed that, in response to the application of the amplification factor signal S21 from the amplification factor selector 107, the relay devices CR1 to CR3 can be selectively activated, or not activated, to select one of the voltage dividing resistors VR1 to VR3 by the respective make contact.

The relationship between the predetermined voltages S24 to S26 and the amplification factor of the amplifier 100 will now be described.

FIG. 5 illustrates a graph showing the relationship between the light transmissivity of the workpiece W and the output signal S3 emerging from the amplifier 100. Curves G1, G2, G3 and G4 shown therein are exhibited when the amplifier 100 is set to have one of the four amplification factors, respectively, and correspond respectively to the levels 1 to 4 hereinbefore discussed. By way of example, the curve G1 is exhibited when the amplification factor of the amplifier 100 is maximum, and corresponds to the output signal S3 within the range of the level 1.

Where the amplification factor is maximum, although the inspection is possible even though the light transmissivity of the workpiece W is extremely low (e.g., about 0.01%), the output signal S3 outputted from the amplifier 100 will be saturated where the light transmissivity is not low (e.g., about 1%) and, therefore, the inspection is not possible. Accordingly, depending on the light transmissivity of the workpiece W detected by means of the sampling operation, one of the curves G1 to G4 appropriate to the detected light transmissivity is selected.

It is to be noted that any one of the curves G2 to G4 can be determined by finding the point of intersection between the imaginary vertical line, which is drawn downwardly from the point of intersection between the curve G1 and the associated predetermined voltage S24 to S26, and a predetermined voltage level, for example, the level of 100 mV and then by shifting the curve G1 rightwards, as viewed in FIG. 5, until the curve G1 passes through the point of intersection between the imaginary vertical line and the predetermined voltage level.

A curve shown by GS in the graph of FIG. 5 represents the intensity of light emitted by the light emitter 12 which is used as the sampling intensity. According to the curve GS, the output signal S3 from the amplifier 100 is lowered approximately by the order of 10 as compared with the curve G1 and the sampling operation takes place under this condition. Therefore, it is possible to accomplish the sampling with respect to the range in which the light transmissivity is not low.

Hereinafter, the inspecting operation will be discussed.

Upon the completion of the sampling operation, the primer coating BP is formed on the workpiece W, followed by the movement of the manipulator to cause the detecting unit 11 to move along the traces of painting used to form the primer coating BP. As the detector unit 11 moves along the painting traces, the output signal S3 emerging from the amplifier 10 varies and is subsequently compared by the comparator 35 with the reference voltage S4.

The reference voltage S4 generated by the reference voltage generator 37 is determined empirically according to results of a series of tests conducted on a suitable number of samples and is, for example, fixed to a value about half the above described voltage level. Thus, in this case, the coating condition in which, consequent upon the formation of the primer coating BP on the workpiece W, the light transmissivity of the workpiece W has been reduced to a value equal to or lower than 50% is deemed satisfactory or acceptable.

Thus, the inspecting apparatus 2 according to the second preferred embodiment of the present invention is so designed that the amplification factor of the amplifier 100 can be stepwisely varied according to the light transmissivity which may in turn vary with the type of the workpiece W, thereby to avoid a possible saturation of the output signal S3 emerging from the amplifier 100. Therefore, even with the ceramics-lined glass having a relatively low light transmissivity, the inspection of the coating condition can be carried out satisfactorily and effectively. Moreover, despite that the reference voltage S4 with which the output signal S3 from the amplifier 100 is compared is fixed, the inspection of the coating condition can be accomplished even with the workpieces W having a relatively wide range of light transmissivity. In addition, the circuit arrangement used in the inspecting apparatus 2 is simple and inexpensive to manufacture.

It is also to be noted that, for the amplifier 100, arrangement may be made that the feedback resistance of an amplifier such as, for example, an operational amplifier, can be selectively chosen according to the amplification factor signal S21 generated from the amplification factor selector 107. Also, although the amplifier 100 has been shown and described as capable of having one of the four amplification factors, the number of the amplification factors to which the amplifier 100 can be set may not be limited to four such as in the illustrated embodiment of FIGS. 3 to 5, but may be equal to or smaller than 3 or equal to or greater than 5. Yet, another amplifier may be interposed between the amplifier 100 and the comparator 35 to amplify the output signal S3 to a higher level and, where such intermediate amplifier is employed, the reference voltage S4 generated from the reference voltage generator 37 has to be of a correspondingly increased value.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, the light emitter 12 may be a light emitting diode, a semiconductor laser or a lamp while the light receiver 4 may be a photodiode, a phototransistor or a charge-coupled device.

Also, any one of the inspecting apparatuses 1 and 2 according to the first and second preferred embodiments of the present invention, respectively, may employ other circuit component parts than those shown and described with reference to the accompanying drawings. Again, the output signal generated from the inspecting apparatus according to any one of the first and second preferred embodiment of the present invention can be used in any suitable manner for accomplishing various controls.

Accordingly, such changes and modifications are, unless they depart from the spirit and scope of the present invention as delivered from the claims annexed hereto, to be construed as included therein.

What is claimed is:

1. A method of inspecting a film-like coating formed on a workpiece, which comprises the steps of:
    positioning the workpiece between a light emitter and a light receiver so that rays of light from the light emitter can pass through the workpiece towards the light receiver;
    amplifying a detection signal generated from the light receiver and being indicative of the amount of light having passed through the workpiece;
    comparing an amplified output signal from the amplifier with a predetermined level with the use of a comparator and generating a control signal from the comparator, which control signal is indicative of a difference between the amplified output signal and the predetermined level;
    adjusting the magnitude of the amplified output signal from the amplifier to a zero value, when and so long as the passage of the rays of light from the light emitter towards the light receiver is intercepted, and also to a predetermined tuned value when and so long as the workpiece placed in position between the light emitter and the light receiver has the coating having not yet been formed thereon, and;
    comparing the amplified output signal, generated from the amplifier when and after the light receiver has detected the rays of light having passed through the workpiece having the coating formed thereon, with the predetermined level by the use of said comparator.

2. An inspecting apparatus for inspecting a film-like coating formed on a workpiece, which comprises:
    a light emitter and a light receiver adapted to be positioned on respective sides of the workpiece, said light receiver generating a detection signal indicative of the amount of light having passed through the workpiece;
    an amplifying means for amplifying the detection signal from the light receiver and for generating an amplified output signal;
    a comparing means for comparing the amplified output signal from the amplifying means with a predetermined level and for generating a control signal indicative of a difference between the amplified output signal and the predetermined level;

a zero adjusting means for adjusting the amplified output signal from the amplifier to a zero value; and a tuning means for tuning the amplified output signal from the amplifier to a predetermined tuned value.

3. The inspecting apparatus as claimed in claim 2, wherein said tuning means comprises an amplification factor adjustment for adjusting the amplification factor of the amplifier, and an emission control means for adjusting the intensity of light emitted by the light emitter towards the light receiver.

4. An inspecting apparatus for inspecting a film-like coating formed on a workpiece, which comprises:

a light emitter and a light receiver adapted to be positioned on respective sides of the workpiece, said light receiver generating a detection signal indicative of the amount of light having passed through the workpiece;

an amplifying means for amplifying the detection signal from the light receiver and for generating an amplified output signal;

an amplification factor setting means for setting one of a plurality of amplification factors to said amplifying means according to the light transmissivity exhibited by the workpiece prior to the formation of the coating on said workpiece; and a comparing means for comparing the amplified output signal from the amplifying means with a reference level and for generating a control signal indicative of a difference between the amplified output signal and the reference level.

* * * * *